United States Patent
Hudak et al.

(10) Patent No.: US 11,179,561 B2
(45) Date of Patent: Nov. 23, 2021

(54) SELF-CURLING COCHLEAR ELECTRODE LEAD AND METHOD OF MANUFACTURING THE SAME

(71) Applicant: Advanced Bionics AG, Staefa (CH)

(72) Inventors: Eric M. Hudak, Los Angeles, CA (US); Anil K. Patnala, Stevenson Ranch, CA (US); Bing Xu, Valencia, CA (US); Timothy Lee Conrad, Pasadena, CA (US); Kurt J. Koester, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 675 days.

(21) Appl. No.: 15/963,808

(22) Filed: Apr. 26, 2018

(65) Prior Publication Data

US 2019/0329027 A1    Oct. 31, 2019

(51) Int. Cl.
*A61N 1/05* (2006.01)
*A61N 1/36* (2006.01)

(52) U.S. Cl.
CPC ....... *A61N 1/0541* (2013.01); *A61N 1/36039* (2017.08)

(58) Field of Classification Search
CPC .............. A61N 1/0541; A61N 1/36038; A61N 1/36039
See application file for complete search history.

(56) References Cited

U.S. PATENT DOCUMENTS

| 5,578,084 A | 11/1996 | Kuzma et al. |
| 5,800,500 A | 9/1998 | Spelman et al. |
| 6,119,044 A | 9/2000 | Kuzma |
| 7,406,352 B2 * | 7/2008 | Gibson ................ A61N 1/0541 607/137 |
| 7,689,260 B2 | 3/2010 | Finch et al. |
| 7,822,487 B2 | 10/2010 | Dadd et al. |

(Continued)

FOREIGN PATENT DOCUMENTS

| KR | 10-0492515 | 6/2005 |
| WO | 2001/012115 | 2/2001 |
| WO | 2011/162912 | 12/2011 |

OTHER PUBLICATIONS

Serrano, et al., Recent Insights Into the Biomedical Applications of Shape-memory Polymers, Macromolecular Journals. Macromol. Biosci. 2012, DOI: 10.1002/mabi.201200097.

(Continued)

*Primary Examiner* — Amanda K Hulbert
(74) *Attorney, Agent, or Firm* — ALG Intellectual Property, LLC

(57) ABSTRACT

An exemplary self-curling cochlear electrode lead includes a flexible body formed of a flexible insulating material, a shape memory polymer element that is embedded within the flexible body and that is configured to cause the self-curling cochlear electrode lead to transition to a curved spiral shape so as to conform with a curvature of a human cochlea when a temperature of the shape memory polymer element reaches a transition temperature, a plurality of electrode contacts arranged along a side of the flexible body, and a plurality of wires embedded within the flexible body and configured to electrically connect the plurality of electrode contacts to at least one signal source. Corresponding methods of manufacturing a self-curling cochlear electrode lead are also described.

11 Claims, 14 Drawing Sheets

(56) References Cited

U.S. PATENT DOCUMENTS

| | | |
|---|---|---|
| 7,974,712 B2 | 7/2011 | Gibson et al. |
| 9,263,172 B2 | 2/2016 | Lotfi |
| 9,446,230 B1 | 9/2016 | Alsheri et al. |
| 2012/0035615 A1 | 2/2012 | Koester et al. |
| 2013/0060260 A1 | 3/2013 | Dudziak et al. |
| 2014/0303642 A2 | 10/2014 | Dudziak et al. |

OTHER PUBLICATIONS

Ware, et al.,Thiol-Click Chemistries for Responsive Neural Interfaces, Macromol. Biosci. 2013, 13, 1640-1647. DOI: 10.1002/mabi.201300272.

Ware, et al.,Thiol-ene/acrylate substrates for softening intracortical electrodes, J Biomed Mater Res Part B 2014:102B:1-11.

\* cited by examiner

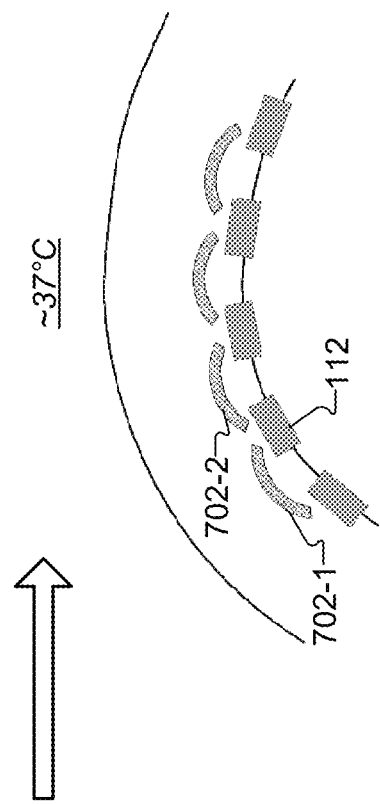
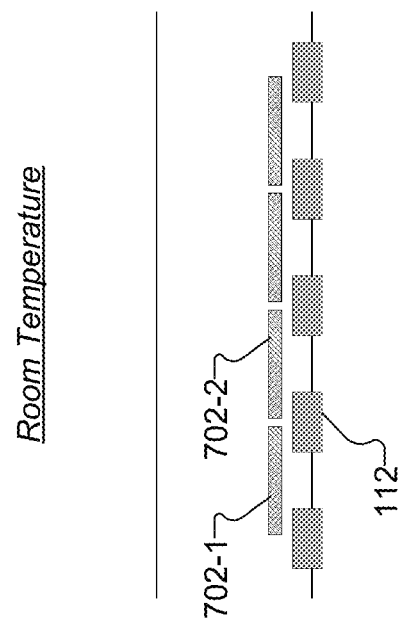

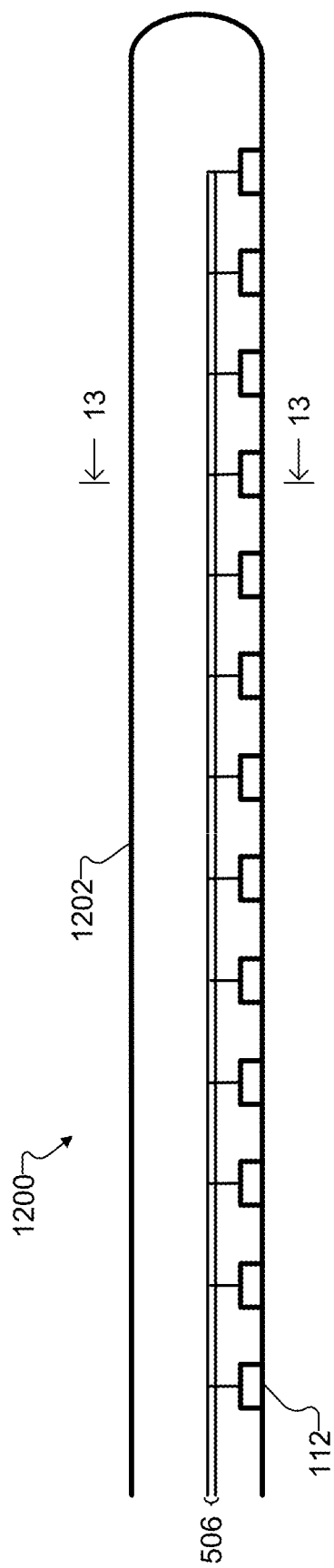

SELF-CURLING COCHLEAR ELECTRODE LEAD AND METHOD OF MANUFACTURING THE SAME

BACKGROUND INFORMATION

Cochlear implant systems are used to provide, restore, and/or improve hearing loss suffered by cochlear implant patients who use the cochlear implant systems. A key component of a cochlear implant system is an electrode lead that is inserted into a cochlea of the patient in a delicate surgical procedure referred to herein as an "insertion procedure." Insertion procedures are difficult due to the structure of the human cochlea, which is in the shape of a spiral beginning at a base and ending at an apex. If the electrode lead is not positioned correctly, cochlear trauma and/or an inferior hearing outcome for the patient may occur.

Current cochlear electrode lead technologies include two general designs: straight cochlear electrode leads and pre-curved cochlear electrode leads. The insertion procedure for straight cochlear electrode leads includes the straight cochlear electrode lead generally following a trajectory of a lateral wall of the scala tympani. Unfortunately, straight cochlear electrode leads have a drawback in that they typically reside far away from the modiolus of the cochlea when inserted, which results in lower specificity in neural activation and a potentially inferior hearing outcome for the patient.

Pre-curved cochlear electrode leads are manufactured in an already-curled shape and are straightened before implantation using either a stylet that is inserted into a lumen of the pre-curved cochlear electrode lead or by using a straight rigid sheath provided around the pre-curved cochlear electrode lead. While a surgeon inserts a pre-curved cochlear electrode lead into the cochlea, the stylet or sheath is gradually withdrawn, which allows the pre-curved cochlear electrode lead to return to its curled shape and conform with the helical shape of the cochlea. Typically, specialized surgical tools and surgical techniques are required to handle the pre-curved cochlear electrode and remove the stylet or sheath. Such techniques can be challenging and require specialized training and experience to perform correctly. Improper insertion of a pre-curved cochlear electrode lead can result in damage to the electrode lead, damage to the cochlear tissue, and/or improper electrode placement in the cochlea (e.g., translocation, tip foldover, etc.). Moreover, typical pre-curved cochlear electrode leads tend to only reach a moderate insertion depth into the cochlea. This results in limited access to more apical spiral ganglion cells that encode low-frequency sounds, a vital component of speech understanding and music appreciation.

Some have proposed using a shape memory alloy such as nitinol to cause a cochlear electrode lead to self-curl upon reaching a transition temperature. However, even though the composition of nitinol may be adjusted to achieve a modulus transition near body temperature, the rate of modulus change cannot be decreased to a useful, optimized rate. This results in an electrode lead that curls too quickly upon insertion into the cochlea and requires the surgeon to match the rate of insertion to the rate of modulus change for the insertion to be successful. If such an electrode lead is inserted too slowly relative to the change in curve of the electrode lead, a tip foldover or a scalar translocation may occur. For at least these reasons, nitinol-based self-curling cochlear electrode leads are unrealistic.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIGS. 8A and 8B illustrate an exemplary transition of the self-curling cochlear electrode lead shown in FIG. 7 from a straightened configuration to a curved configuration when inserted into the cochlea according to principles described herein.

FIG. 12 illustrates an additional exemplary self-curling cochlear electrode lead in which an entire flexible portion of the self-curling cochlear electrode lead is formed of a shape memory polymer according to principles described herein.

DETAILED DESCRIPTION

Figure 1:
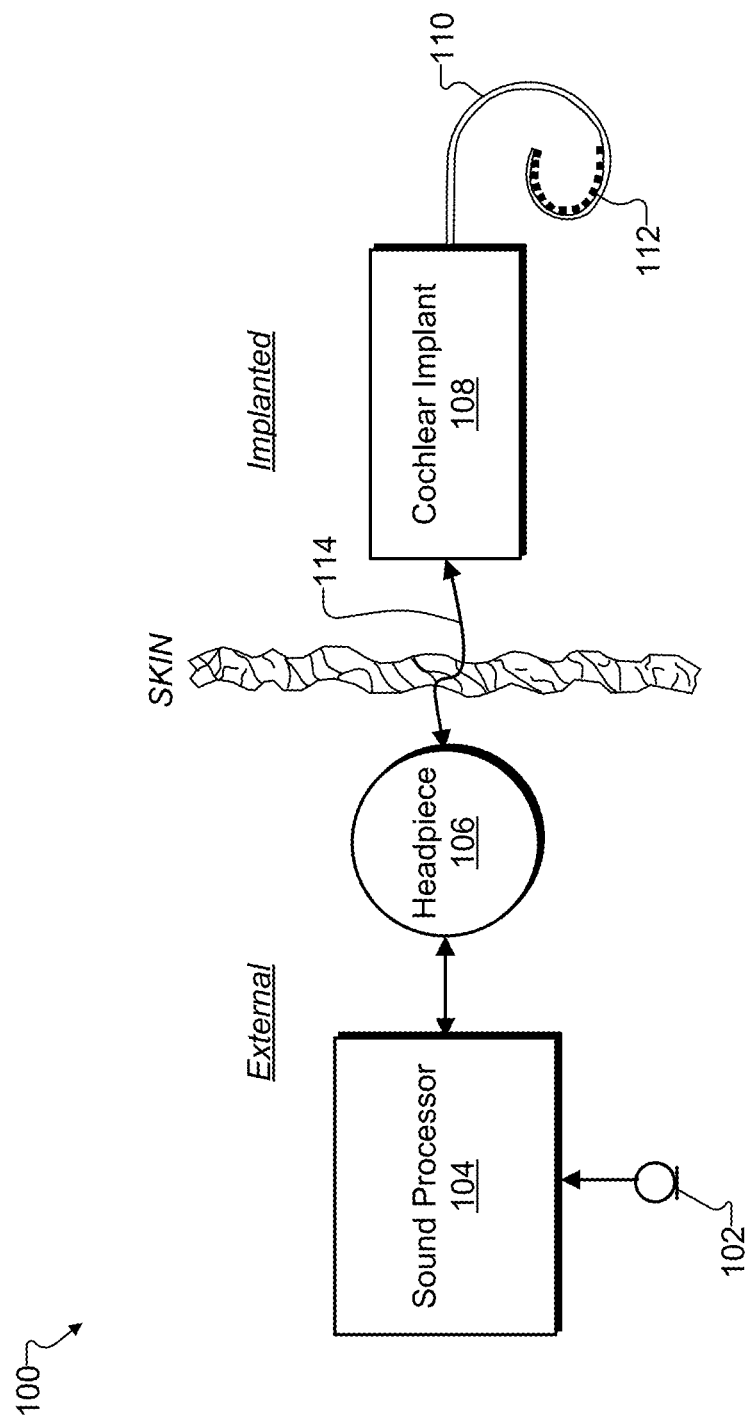
FIG. 1 illustrates an exemplary cochlear implant system according to principles described herein.

A self-curling cochlear electrode lead and methods for manufacturing the same are described herein. To overcome the aforementioned problems, the self-curling cochlear electrode leads described herein are configured to both self-curl to a mid-scalar or perimodiolar position and also extend more apically into the cochlea after insertion to gain access to low-frequency spiral ganglion cells. The exemplary self-curling cochlear electrode leads described herein achieve these goals by employing designs that have optimal self-curling properties and/or advantageous methods of curling.

As will be described in more detail below, the exemplary self-curling cochlear electrode leads described herein may include a plurality of electrode contacts, a plurality of wires connected to the plurality of electrode contacts, and a portion that includes a shape memory polymer that causes the cochlear electrode lead to transition (e.g., from a substantially straightened position) to a curved spiral shape so as to conform with a curvature of a human cochlea. As used herein, a "shape memory polymer" refers to a type of polymeric material that has the ability to transition from a temporary shape (e.g., a substantially straight shape) to a permanent shape in response to an external stimulation, such as the application of heat. The shape memory polymers described herein are configured to transition to a curved spiral shape when a temperature of the shape memory polymer reaches a transition temperature. As used herein, the "transition temperature" refers to the temperature at which the shape memory polymer transitions to its permanent shape from the temporary shape. Examples of shape memory polymers and how shape memory polymers may cause a self-curling cochlear electrode lead to transition to a curved spiral shape are described herein.

The self-curling cochlear electrode leads described herein may provide various benefits to cochlear implant patients, as well as to surgeons and others involved with insertion procedures. For example, because the cochlear electrode leads described herein self-curl, a surgeon is able to insert the self-curling cochlear electrode lead in a manner that does not require a specialized insertion tool and/or an advanced insertion technique. In addition, self-curling cochlear electrode leads such as those described herein are configured to be stiff enough to maintain a substantially straight configuration before being inserted into the cochlea, but compliant enough while in the straight configuration to flex to some degree when inserted into the cochlea in order to minimize or prevent damage to the cochlea as the self-curling cochlear electrode leads come into contact with walls and/or other structures of the cochlea. Further, self-curling cochlear electrode leads such as those described herein may beneficially travel along the lateral wall of the scala tympani upon initial insertion into the cochlea, move toward the modiolus at a pre-defined rate after insertion into the cochlea, extend more toward the apex of the cochlea than conventional pre-curved cochlear electrode leads, and employ optimal self-curling characteristics that ensure the cochlear electrode lead progresses in a desirable trajectory. Moreover, the self-curling cochlear electrode leads described herein may not include a lumen that is configured to receive a stylet. Because of this, it may be possible to make self-curling cochlear electrode leads such as those described herein thinner than conventional pre-curved cochlear electrode leads, which increases the likelihood of having an atraumatic insertion into the cochlea.

In addition, the methods of manufacturing a self-curling cochlear electrode lead described herein are beneficial in that they simplify the manufacturing process and/or reduce manufacturing costs as compared to manufacturing conventional pre-curved cochlear electrode leads. Conventional pre-curved cochlear electrode leads are typically formed using a cochlear electrode lead mold that includes a portion designed to form a lumen that has a specific shape and dimensions. Changing the shape and dimensions of the lumen in a conventional pre-curved cochlear electrode lead typically requires manufacturing a new cochlear electrode lead mold, which is costly and time consuming. In contrast, because the self-curling cochlear electrode leads described herein do not position the shape memory polymer within a lumen, there is no need to design the shape memory polymer to fit within a specific lumen. In addition, with the self-curling cochlear electrode leads described herein, the design of the shape memory polymer can be changed without having to manufacture a new cochlear electrode lead mold, which results in reduced manufacturing costs. Further, the methods of manufacturing a self-curling cochlear electrode lead described herein do not require multiple polymer components to be assembled or adhered together, which results in a simplified manufacturing process.

Various embodiments will now be described in more detail with reference to the figures. The disclosed apparatus and methods may provide one or more of the benefits mentioned above and/or various additional and/or alternative benefits that will be made apparent herein.

FIG. 1 illustrates an exemplary cochlear implant system 100. As shown, cochlear implant system 100 may include a microphone 102, a sound processor 104, a headpiece 106 having a coil disposed therein, a cochlear implant 108, and a self-curling cochlear electrode lead 110 ("electrode lead 110"). Electrode lead 110 may include an array of electrodes 112 disposed on a distal portion of electrode lead 110 and that are configured to be inserted into the cochlea to stimulate the cochlea after the distal portion of electrode lead 110 is inserted into the cochlea. It will be understood that one or more other electrodes (e.g., including a ground electrode, not explicitly shown) may also be disposed on other parts of electrode lead 110 (e.g., on a proximal portion of electrode lead 110) to, for example, provide a current return path for stimulation current generated by electrodes 112 and to remain external to the cochlea after electrode lead 110 is inserted into the cochlea. Various embodiments of self-curling cochlear electrode lead 110 will be described herein. Additional or alternative components may be included within cochlear implant system 100 as may serve a particular implementation. For example, a pre-curved electrode lead and/or a straight electrode lead may alternatively be used in connection with cochlear implant 108.

As shown, cochlear implant system 100 may include various components configured to be located external to a patient including, but not limited to, microphone 102, sound processor 104, and headpiece 106. Cochlear implant system 100 may further include various components configured to be implanted within the patient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a device like the Clinical Programming Interface ("CPI") device from Advanced Bionics, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, headpiece 106, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108 (e.g., a wireless link between a coil disposed within headpiece 106 and a coil physically coupled to cochlear implant 108). It will be understood that communication link 114 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the patient via electrodes 112 disposed along electrode lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

Figure 2:
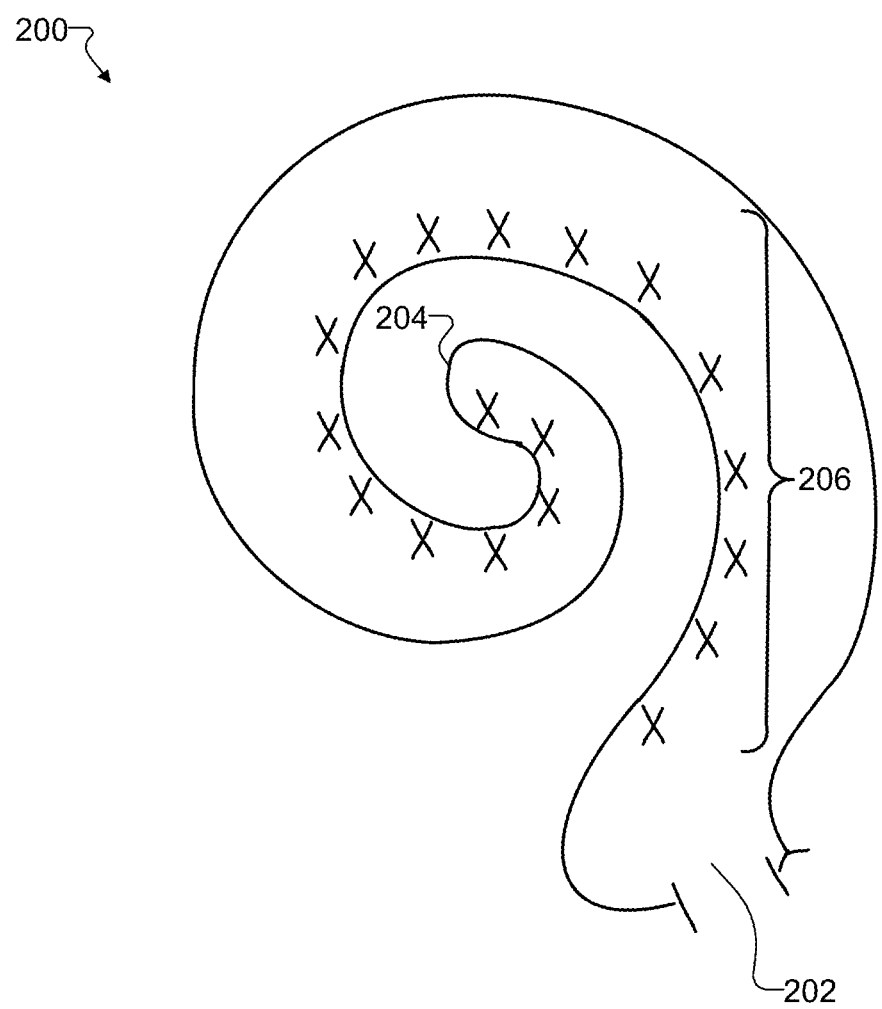
FIG. 2 illustrates a schematic structure of the human cochlea according to principles described herein.

FIG. 2 illustrates a schematic structure of the human cochlea 200 into which electrode lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the electrode lead, the anatomy of the patient's cochlea, and/or any other factor as may serve a particular implementation.

Figure 3:
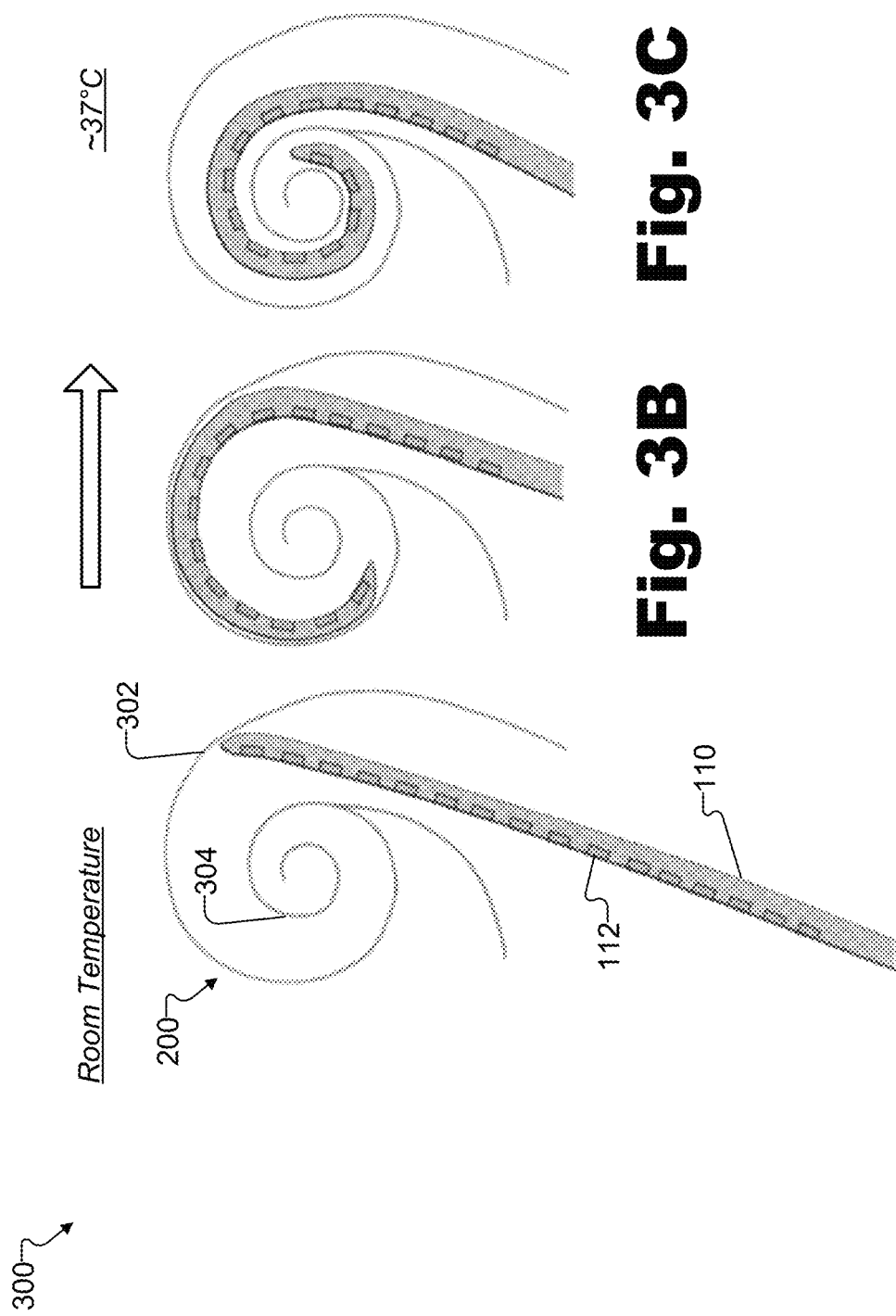
FIGS. 3A-3C illustrate an exemplary insertion procedure of a self-curling cochlear electrode lead according to principles described herein.

FIGS. 3A-3C illustrate an exemplary insertion procedure 300 that shows how self-curling cochlear electrode lead 110 may transition from a straight configuration to a curved configuration upon insertion in cochlea 200. Prior to self-curling cochlear electrode lead 110 being inserted into the patient's cochlea, self-curling cochlear electrode lead 110 may be heated, bent into the straight configuration, and allowed to cool to the transition temperature while being held in the straight configuration. Self-curling cochlear electrode lead 110 may be configured to maintain the straight configuration at room temperature (e.g., approximately 23° C.) but transition to the curved configuration once self-curling cochlear electrode lead 110 reaches the transition temperature. The transition temperature of self-curling cochlear electrode lead 110 may be any suitable temperature that is above room temperature but that is at or below a normal body temperature of the patient (e.g., approximately 37° C.).

As illustrated in FIG. 3A, insertion procedure 300 may involve inserting self-curling cochlear electrode lead 110 while in the straight configuration through an entry point (e.g., within a round window or cochleostomy of cochlea 200, or another suitable location) and into a scala tympani of cochlea 200. Self-curling cochlear electrode lead 110 may be sufficiently compliant that, as the insertion of self-curling cochlear electrode lead 110 proceeds, self-curling cochlear electrode lead 110 may follow, as shown in FIG. 3B, a lateral wall 302 of the scala tympani without causing damage to cochlea 200. Once self-curling cochlear electrode lead 110 reaches the transition temperature, the shape memory polymer causes self-curling cochlear electrode lead 110 to transition to the curved configuration in which self-curling cochlear electrode lead 110 has a curved spiral shape that conforms with a curvature of cochlea 200. As shown in FIG. 3C, the change in temperature causes self-curling cochlear electrode lead 110 to self-curl away from lateral wall 302 and toward the modiolus 304 of cochlea 200. In so doing, self-curling cochlear electrode lead 110 is also able to extend more toward the apex of cochlea 200 than traditional pre-curved cochlear electrode leads.

The shape memory polymer used in self-curling cochlear electrode lead 110 may include any suitable polymer that is configured to transition from a temporary shape (e.g., a straightened configuration) to its permanent shape once the shape memory polymer reaches the transition temperature.

Examples of shape memory polymers that may be utilized in self-curling cochlear electrode leads such as those described herein may include, for example, polyurethanes, polynorbornene, poly(ε-caprolactone) combined with poly(hydroxybutyrate-co-hydroxyvalerate), and/or any other suitable shape memory polymer or combination of shape memory polymers.

Figure 4:
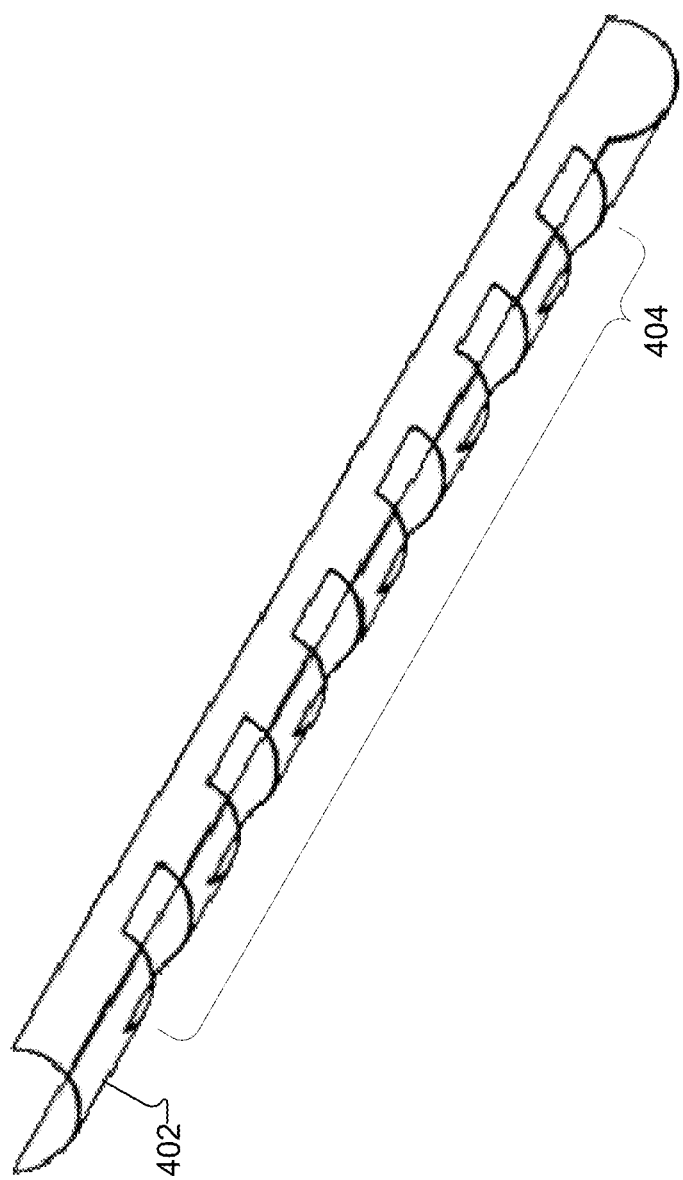
FIG. 4 illustrates an exemplary shape memory polymer element according to principles described herein.

A shape memory polymer may be incorporated in or form part of a self-curling cochlear electrode lead in any suitable manner. In certain examples, shape memory polymer may be incorporated in a self-curling cochlear electrode lead in the form of a shape memory polymer element that includes a plurality of through-holes spaced apart along a longitudinal direction of the shape memory polymer element. To illustrate, FIG. 4 shows an exemplary shape memory polymer element 402 that may be embedded within a self-curling cochlear electrode lead according to one embodiment. As shown in FIG. 4, shape memory polymer element 402 includes a plurality of through-holes 404 provided along the longitudinal direction of shape memory polymer element 402. The example shown in FIG. 4 includes six through-holes 404. However, any suitable number of through-holes may be provided in shape memory polymer element 402 as may suit a particular implementation. In addition, each of the plurality of through-holes 404 shown in FIG. 4 has a rectangular shape. However, any other suitable shape (e.g., circular, oval, square, etc.) or combination of shapes of through-holes may be provided in other implementations.

In certain examples, there may be a one-to-one correspondence of through-holes 404 and electrode contacts included in a self-curling cochlear electrode lead. Alternatively, a single through-hole 404 may be provided at a position corresponding to two or more electrode contacts included in a self-curling cochlear electrode lead.

In certain examples, through-holes 404 may facilitate a more controlled self-curling cochlear electrode lead manufacturing process. For example, during the manufacturing process, a manufacturer of a self-curling cochlear electrode lead may place shape memory polymer element 402 within a cochlear electrode lead mold and then utilize through-holes 404 in shape memory polymer element 402 as guides to correctly position and align each electrode contact within the cochlear electrode lead mold.

In the example shown in FIG. 4, shape memory polymer element 402 is formed in the shape of a channel having a "U" shaped cross-section. Each through-hole included in plurality of through-holes 404 may be arranged in a line in the longitudinal direction of shape memory polymer element 402.

Figure 5:
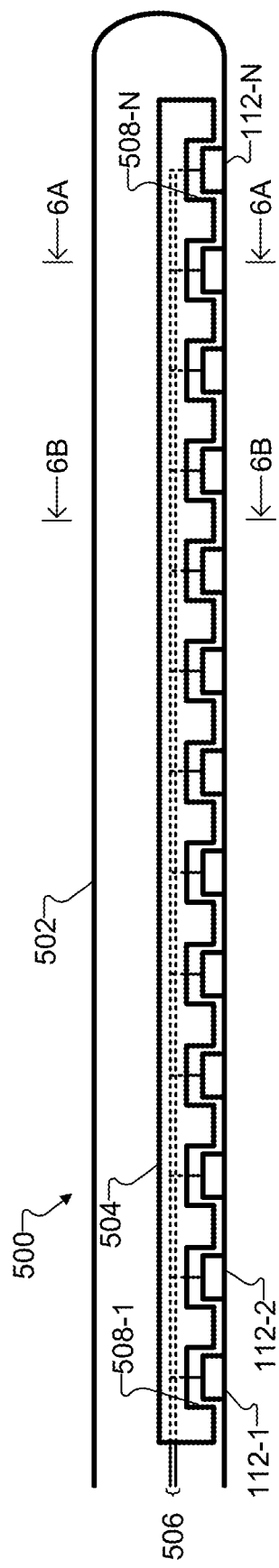
FIG. 5 illustrates an exemplary configuration of a self-curling cochlear electrode lead that includes a shape memory polymer element similar to the one illustrated in FIG. 4 according to principles described herein.

Because shape memory polymer element 402 is formed in the shape of a channel, shape memory polymer element 402 may be configured to guide wires included in the cochlear electrode lead to respective electrode contacts. To illustrate, FIG. 5 shows an exemplary self-curling cochlear electrode lead 500 according to an embodiment that incorporates a shape memory polymer element similar to the one illustrated in FIG. 4. As shown in FIG. 5, self-curling cochlear electrode lead 500 includes a flexible body 502, a shape memory polymer element 504 that is embedded within flexible body 502, a plurality of electrode contacts 112 (e.g., electrode contacts 112-1 through 112-N) arranged along a side of flexible body 502, and a plurality of wires 506 that are embedded within flexible body 502 and that are configured to electrically connect plurality of electrode contacts 112 to at least one signal source (e.g., sound processor 104).

Flexible body 502 may be formed of any suitable biocompatible insulating material that is sufficiently flexible to bend and follow lateral wall 302 of the scala tympani and to further bend when shape memory polymer element 504 reaches its transition temperature. In certain examples, flexible body 502 may be formed of silicone. However, any other suitable insulating material may be used in certain implementations.

Similar to shape polymer element 402, shape polymer element 504 includes a plurality of through-holes 508 (e.g., through-holes 508-1 through 508-N). As shown in FIG. 5, a position of each electrode contact included in plurality of electrode contacts 112 corresponds to a respective through-hole included in the plurality of through-holes 508 of shape memory polymer element 504.

Figure 6:
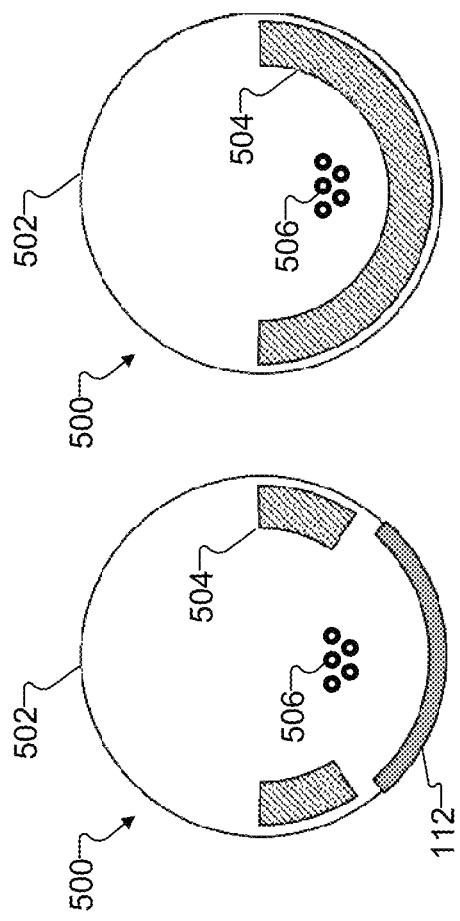
FIGS. 6A and 6B illustrate exemplary cross sections of the self-curling cochlear electrode lead shown in FIG. 5 that are taken along lines 6A and 6B in FIG. 5 according to principles described herein.

FIGS. 6A and 6B depict cross-sectional views at lines 6A and 6B, respectively, of self-curling cochlear electrode lead 500 shown in FIG. 5. As shown in FIGS. 6A and 6B, self-curling cochlear electrode lead 500 does not include a lumen that is configured to receive a stylet. Rather, shape memory polymer element 504 may be embedded within electrode lead 500 such that flexible body 502 completely surrounds shape memory polymer element 504.

The exemplary shape memory polymer elements shown in FIGS. 4 and 5 include a single continuous structure for the shape memory polymer element. However, in certain alternative examples, self-curling cochlear electrode leads such as those described herein may include a plurality of shape memory polymer elements that are embedded within a flexible body but that are separate from each other. For example, the plurality of shape memory polymer elements may include a first shape memory polymer element and a second shape memory polymer element that are spaced apart from each other along a longitudinal direction of the cochlear electrode lead. In certain examples, the first shape memory polymer element and the second shape memory polymer element may have a same transition temperature (e.g., approximately 37° C.) but may have different lengths, cross-sections, and/or other material properties. For example, the first shape memory polymer element may have a different curling rate than the second shape memory polymer element. By including multiple shape memory polymer elements with different curling rates in a self-curling cochlear electrode lead, it may be possible to specifically design different portions of the self-curling cochlear electrode lead to curl at pre-defined rates. To illustrate, a distalmost shape memory polymer element in a self-curling cochlear electrode lead typically has to travel a greater distance when transitioning from the straight configuration to the curved configuration. Accordingly, the distalmost shape memory polymer element may be designed to have a higher curling rate than a shape memory polymer element positioned more proximal on the self-curling cochlear electrode lead. Alternatively, the distalmost shape memory polymer element may be designed to have a slower curling rate than a shape memory polymer element positioned more proximal on the self-curling cochlear electrode lead.

Figure 7:
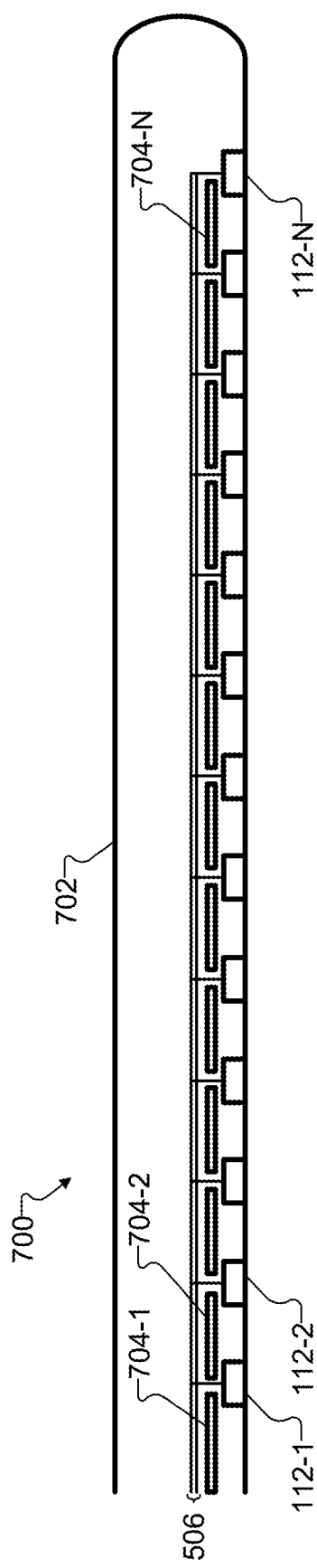
FIG. 7 illustrates an exemplary self-curling cochlear electrode lead that includes a plurality of shape memory polymer elements according to principles described herein.

A self-curling cochlear electrode lead may include any number of shape memory polymer elements as may suit a particular implementation. FIG. 7 illustrates an exemplary self-curling electrode lead 700 that includes a flexible body 702, which is formed of flexible insulating material, and a plurality of shape memory polymer elements 704 (e.g., shape memory polymer elements 704-1 through 704-N) embedded within flexible body 702. In FIG. 7, plurality of shape memory polymer elements 704 are shown for simplicity as having a rectangular side surface. However, plurality of shape memory polymer elements 704 may have any suitable shape or combination of different shapes as may suit a particular implementation.

In certain examples, a length of the first shape memory polymer element may span two or more adjacent electrode contacts included in the plurality of electrode contacts and a length of the second shape memory polymer element may span two or more additional adjacent electrode contacts included in the plurality of electrode contacts. In the example shown in FIG. 7, a single shape memory polymer element 704 partially spans each adjacent electrode contact 112.

FIGS. 8A and 8B illustrate simplified partial diagrams showing how self-curling cochlear electrode lead 700 shown in FIG. 7 may transition from a straight configuration to a curved configuration. As shown in FIG. 8A, at room temperature, first shape memory polymer element 704-1 and second shape memory polymer element 704-2 are in a first state that allows self-curling cochlear electrode lead 700 to have a straight configuration. As the temperature of self-curling cochlear electrode lead 700 reaches the transition temperature (e.g., approximately 37° C.), each of plurality of shape memory polymer elements 704 changes shape, which exerts a force on flexible body 702 and causes self-curling cochlear electrode lead 700 to transition to a curved spiral shape so as to conform with a curvature of the human cochlea.

Figure 9:
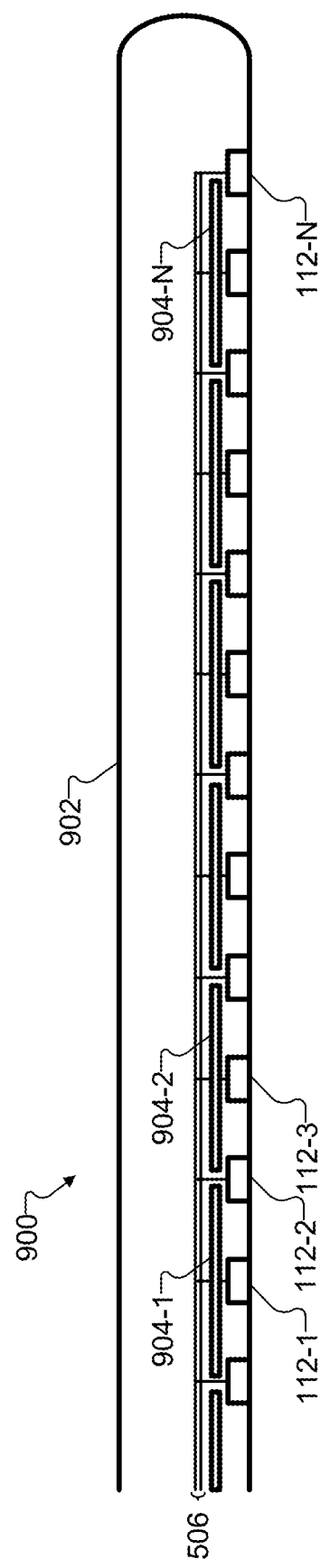
FIGS. 9 and 10 illustrate additional exemplary embodiments of a self-curling cochlear electrode lead that include a plurality of shape memory polymer elements according to principles described herein.

In other examples, a length of the first shape memory polymer element may completely span a first electrode contact included in the plurality of electrode contacts and may partially span a second electrode contact included in the plurality of electrode contacts. A length of the second shape memory polymer element may partially span the second electrode contact and completely span a third electrode contact included in the plurality of electrode contacts. To illustrate, FIG. 9 shows an exemplary self-curling cochlear electrode lead 900 that includes a flexible body 902, a plurality of shape memory polymer elements 904 (e.g., shape memory polymer elements 904-1 through 904-N), wires 506, and electrode contacts 112. Flexible body 902, wires 506, and electrode contacts 112 are arranged in a manner similar to self-curling cochlear electrode lead 700 shown in FIG. 7. However, the embodiment shown in FIG. 9 differs in that the length of each of the shape memory polymer elements 904 shown in FIG. 9 is relatively longer in the lateral direction (i.e., a horizontal direction in FIG. 9) than those shown in FIG. 7. As shown in FIG. 9, shape memory polymer element 902-1 completely spans electrode contact 112-1 and partially spans electrode contact 112-2, which is directly adjacent electrode contact 112-1. Shape memory polymer element 904-2 partially spans electrode contact 112-2 and completely spans electrode contact 112-3, which is directly adjacent to electrode contact 112-2.

Figure 10:
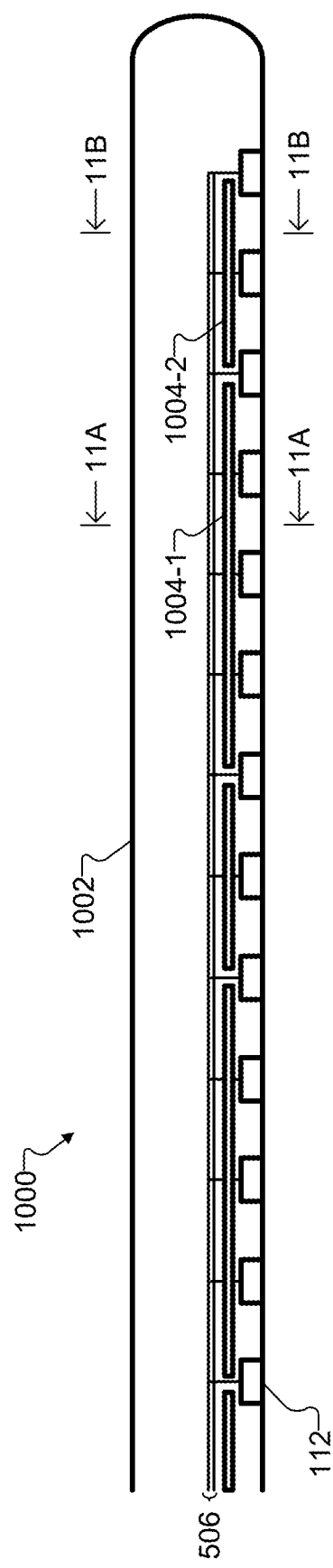

In the embodiments shown in FIGS. 7 and 9, the length of each of the shape memory polymer elements are shown as being substantially equal. However, in certain examples, at least two or all of the shape memory polymer elements may have different lengths in the longitudinal direction of the self-curling cochlear electrode lead. To illustrate, FIG. 10 shows an exemplary self-curling cochlear electrode lead that includes a flexible body 1002, wires 506, and electrode contacts 112. As shown in FIG. 10, a plurality of shape memory polymer elements 1004 (e.g., shape memory polymer elements 1004-1 through 1004-N) are embedded within flexible body 1002. However, at least some of shape memory polymer elements 1004 have a different length in the longitudinal direction than others. For example, shape memory polymer element 1004-1 is relatively longer in the longitudinal direction than shape memory polymer element 1004-2.

Additionally or alternatively, the first shape memory polymer element may have a different modulus of elasticity at the transition temperature than the second shape memory polymer element. For example, shape memory polymer element 1004-2, which is provided at the distal end of self-curling cochlear electrode lead 1000, may have a lower modulus of elasticity than one or more other shape memory polymer elements included in self-curling cochlear electrode lead 1000 because shape memory polymer element 1004-2 may have to bend more than the other shape memory polymer elements for self-curling cochlear electrode lead 1000 to sufficiently conform to the curvature of the cochlea.

Figure 11A:
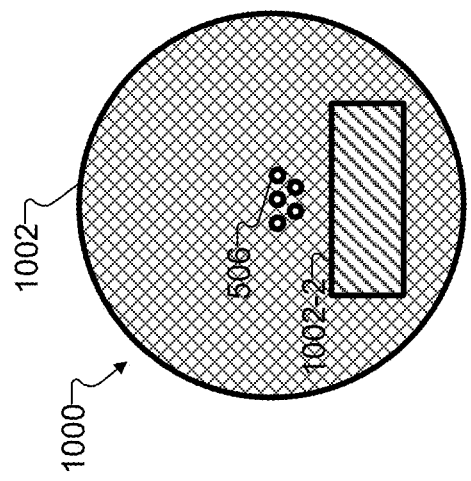
FIGS. 11A and 11B illustrate exemplary cross sections of the self-curling cochlear electrode lead shown in FIG. 10 that are taken along lines 11A and 11B in FIG. 10 according to principles described herein
Figure 11B:
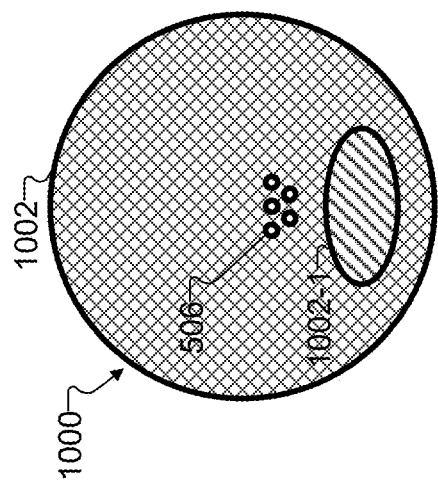

Additionally or alternatively, two or more shape memory polymer elements may have different cross-sectional shapes when viewed in a cross section that is perpendicular to the longitudinal direction of the cochlear electrode lead. To illustrate, FIGS. 11A and 11B depict cross-sectional views at lines 11A and 11B, respectively, of self-curling cochlear electrode lead 1000 shown in FIG. 10. As shown in FIGS. 11A and 11B, shape memory polymer element 1002-1 may have an oval cross-sectional shape whereas shape memory polymer element 1002-2 may have a rectangular cross-sectional shape. The cross-sectional shapes shown in FIGS. 11A and 11B are merely provided for illustrative purposes. It is understood that shape memory polymer elements may have any suitable cross-sectional shape as may suit a particular implementation.

The exemplary self-curling cochlear electrode leads shown, for example, FIGS. 5, 7, and 9 include one or more shape memory polymer elements embedded in a flexible body. However, in certain examples, a self-curling cochlear electrode lead may include a flexible body that is formed entirely of a shape memory polymer. To illustrate, FIG. 12 shows a self-curling cochlear electrode lead 1200 that only includes a flexible body 1202 formed entirely of a shape memory polymer, electrode contacts 112 spaced apart along a first side of flexible body 1202, and wires 504 embedded within flexible body 1202 and configured to electrically connect the electrode contacts 112 to at least one signal source (e.g., sound processor 104).

Flexible body 1202 may be formed of any suitable shape memory polymer, such as those described herein. Similar to the other embodiments described herein, self-curling cochlear electrode lead 1200 does not include a lumen configured to receive a stylet. In addition, flexible body 1202 does not include silicone or layers of other materials. Accordingly, in the embodiment shown in FIG. 12, there is no need for an adhesion layer to be provided between a shape memory polymer and another layer.

Figure 13A:
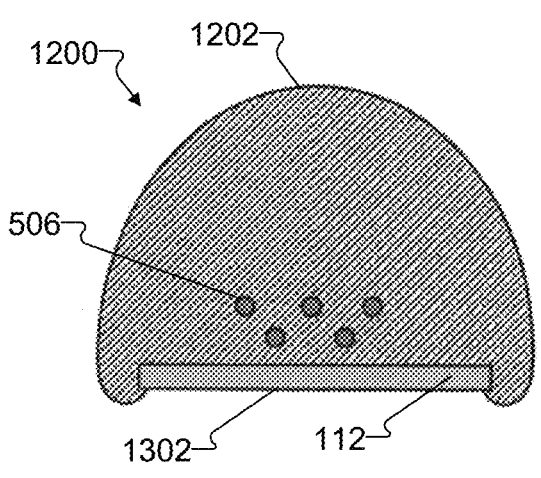
FIGS. 13A and 13B illustrate exemplary alternative cross sections of the self-curling cochlear electrode lead shown in FIG. 12 that may be taken along lines 13 in FIG. 12 according to principles described herein.
Figure 13B:
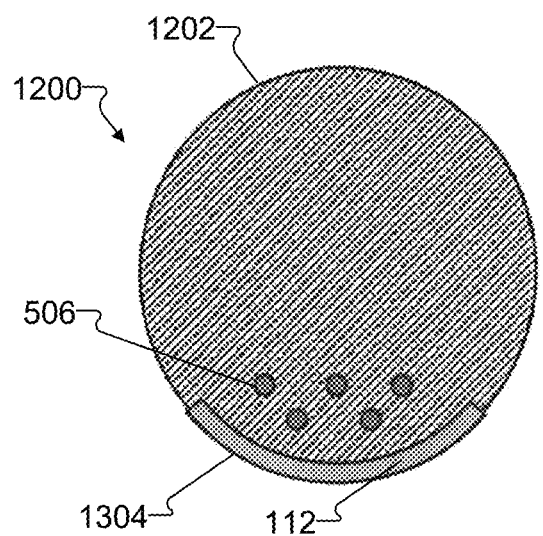

In certain examples, self-curling cochlear electrode leads such as those described herein may have electrode contacts with flat externally facing surfaces. Alternatively, certain self-curling cochlear electrode leads may have electrode contacts with curved externally facing surfaces. To illustrate, FIGS. 13A and 13B show alternative cross-sectional views that may be observed at line 13 in FIG. 12. As shown in FIG. 13A, self-curling cochlear electrode lead 1200 may include at least one electrode contact 112 that has a flat externally facing surface 1302. In an alternative embodiment shown in FIG. 13B, self-curling cochlear electrode lead 1200 may include at least one electrode contact 112 that has a curved externally facing surface 1304.

Figure 14:
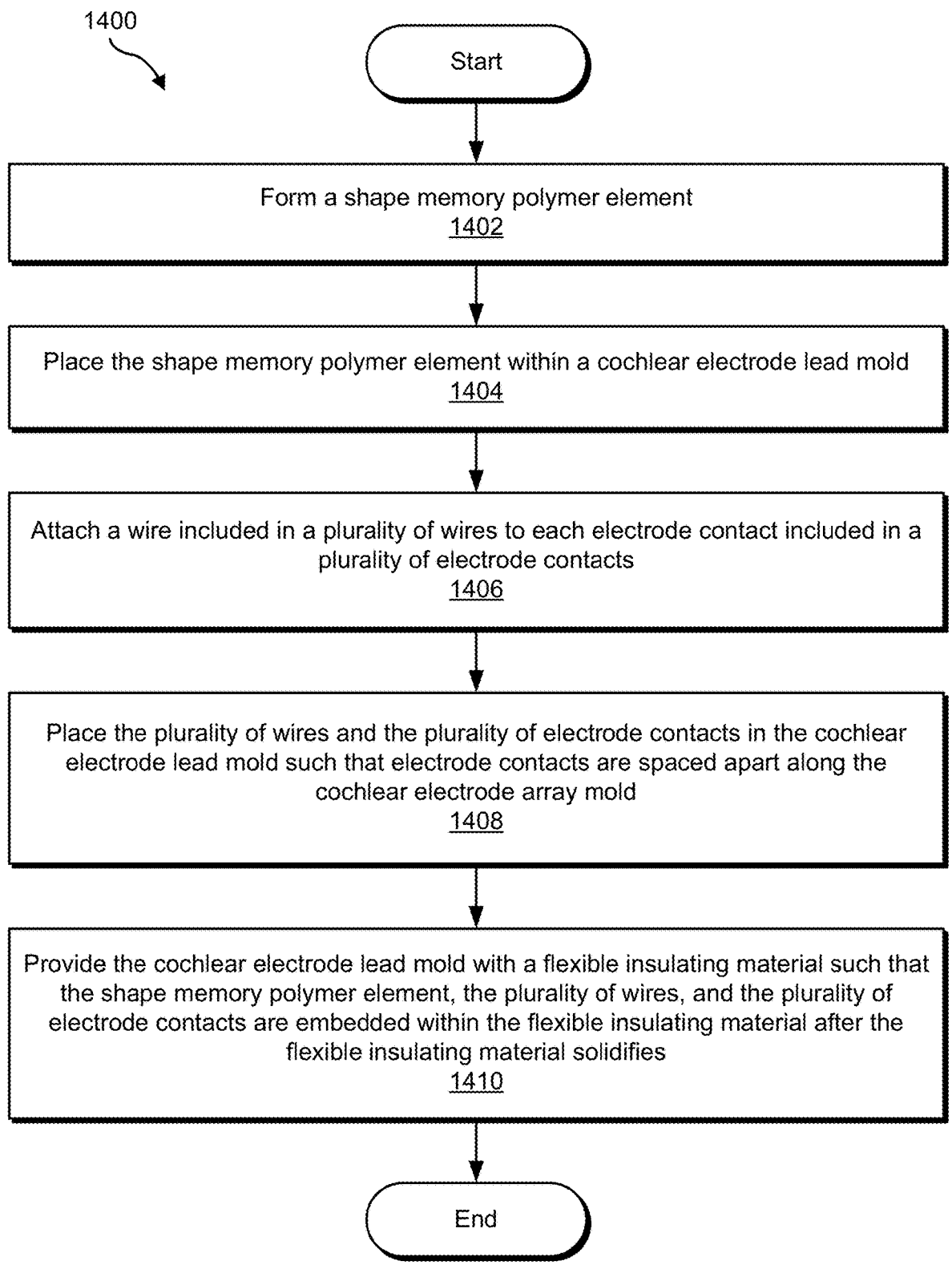
FIG. 14 shows an exemplary method for manufacturing a self-curling cochlear electrode lead according to principles described herein.

FIG. 14 illustrates a method 1400 for manufacturing a self-curling cochlear electrode lead (e.g., self-curling cochlear electrode lead 110). While FIG. 14 illustrates exemplary operations according to one embodiment, other embodiments may omit, add to, reorder, and/or modify any of the operations shown in FIG. 14.

In operation 1402, a shape memory polymer element is formed in any suitable manner. In certain examples, the shape memory polymer element may be formed so as to include a plurality of through-holes spaced apart along a longitudinal direction of the shape memory polymer element. Alternatively, the shape memory polymer element may be formed so as to include a plurality of shape memory polymer elements, such as described herein. Operation 1402 may be performed in any of the ways described herein.

In operation 1404, the shape memory polymer element is placed in a cochlear electrode lead mold. The cochlear electrode lead mold may have any suitable configuration. In certain examples, the cochlear electrode lead mold may be a straight mold in which each of the plurality of electrode contacts are positioned in a straight line. Alternatively, the cochlear electrode lead mold may be a curved mold that has a curvature that conforms with the curvature of the human cochlea. Operation 1404 may be performed in any of the ways described herein.

In operation 1406, a wire included in the plurality of wires is attached to each electrode contact included in a plurality of electrode contacts. The wire may be attached in any suitable manner. For example, a wire may be welded to each electrode contact included in the plurality of electrode contacts. Operation 1406 may be performed in any of the ways described herein.

In operation 1408, the plurality of wires and the plurality of electrode contacts are placed in the cochlear electrode lead mold such that the electrode contacts are spaced apart along the cochlear electrode lead mold. Operation 1408 may be performed in any of the ways described herein.

In operation 1410, the cochlear electrode lead mold is provided with a flexible insulating material such that the shape memory polymer element, the plurality of wires, and the plurality of electrode contacts are embedded within the flexible insulating material after the flexible insulating material solidifies. The cochlear electrode lead mold may be provided with the flexible insulating material in any suitable manner. In certain examples, the flexible insulating material may be injected into the cochlear electrode lead mold such that the flexible insulating material embeds the shape memory polymer element, the plurality of wires, and the plurality of electrode contacts. Alternatively, the flexible insulating material may be compression molded in the cochlear electrode lead mold (e.g., by providing the flexible insulating material in a first half of the cochlear electrode lead mold and then pressing a second half of the cochlear electrode lead mold onto the flexible insulating material provided in the first half of the cochlear electrode lead mold). Operation 1410 may be performed in any of the ways described herein.

In certain examples, operation 1404 may be performed prior to operation 1408. Such an order of operations may be beneficial in certain examples where the cochlear electrode lead includes a shape memory polymer element that includes a plurality of through-holes. Alternatively, operation 1404 may be performed subsequent to or concurrently with operation 1408 as may serve a particular implementation. When the shape memory polymer element includes a plurality of through-holes, the method may further include utilizing the plurality of through-holes in the shape memory polymer element to position each of the plurality of electrode contacts and align the plurality of electrode contacts for connecting to the plurality of wires, and utilizing the shape memory polymer element to route the plurality of wires along a longitudinal direction of the shape memory polymer element.

In examples where a curved cochlear electrode lead mold is used, the method may further comprise removing the self-curling cochlear electrode lead from the cochlear electrode lead mold, heating the self-curling cochlear electrode lead above the transition temperature, straightening the self-curling cochlear electrode lead, and providing the self-curling cochlear electrode lead within packaging that includes one or more fixing elements (e.g., a specifically designed groove and/or a rigid sheath) configured to hold the self-curling cochlear electrode lead in a straightened state. Because the physical movement of the self-curling cochlear electrode lead may be restricted in such a manner, the self-curling cochlear electrode lead will not curl during sterilization, shipping, and unpacking in the operating room, even if the temperature of the self-curling cochlear electrode lead exceeds the transition temperature during that time. As long as the temperature of the self-curling cochlear electrode lead is below the transition temperature when it is removed from the packaging, it will remain in the straightened configuration and not self-curl until it is inserted in the cochlea by the surgeon. In so doing, the surgeon may more easily insert the self-curling cochlear electrode lead because it is not necessary to go through the lengthy process of straightening the self-curling cochlear electrode lead in the operating room.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A self-curling cochlear electrode lead adapted for insertion into a human cochlea, comprising:
   a flexible body formed of a flexible insulating material;
   a shape memory polymer element that is embedded within and completely surrounded by the flexible body and that is configured to cause the cochlear electrode lead to transition to a curved spiral shape so as to conform with a curvature of the human cochlea when a temperature of the shape memory polymer element reaches a transition temperature, the shape memory polymer element including a plurality of through-holes spaced apart along a longitudinal direction of the shape memory polymer element;
   a plurality of electrode contacts arranged along a side of the flexible body, a position of each electrode contact included in the plurality of electrode contacts corresponding to a respective through-hole included in the plurality of through-holes; and
   a plurality of wires embedded within the flexible body and configured to electrically connect the plurality of electrode contacts to at least one signal source.

2. The self-curling cochlear electrode lead of claim 1, wherein the shape memory polymer element is in the shape of a channel and each through-hole included in the plurality of through-holes is arranged in a line in the longitudinal direction of the shape memory polymer element.

3. The self-curling cochlear electrode lead of claim 2, wherein the channel is configured to guide the plurality of wires along the longitudinal direction of the shape memory polymer element.

4. The self-curling cochlear electrode lead of claim 1, wherein the flexible body does not include a lumen configured to receive a stylet.

5. The self-curling cochlear electrode lead of claim 1, wherein the shape memory polymer element has a U-shape when viewed in cross-section.

6. A self-curling cochlear electrode lead adapted for insertion into a human cochlea, comprising:
    a flexible body formed of a flexible insulating material;
    a plurality of shape memory polymer elements embedded within the flexible body and configured to cause the cochlear electrode lead to transition to a curved spiral shape so as to conform with a curvature of the human cochlea when a temperature of the plurality of shape memory polymer elements reaches a transition temperature, the plurality of shape memory polymer elements including a first shape memory polymer element and a second shape memory polymer element that are spaced apart from each other along a longitudinal direction of the cochlear electrode lead, the first shape memory polymer element and the second shape memory polymer element having a same transition temperature but having different curling rates;
    a plurality of electrode contacts arranged along a side of the flexible body; and
    a plurality of wires embedded within the flexible body and configured to electrically connect the plurality of electrode contacts to at least one signal source.

7. The self-curling cochlear electrode lead of claim 6, wherein:
    a length of the first shape memory polymer element spans two or more adjacent electrode contacts included in the plurality of electrode contacts; and
    a length of the second shape memory polymer element spans two or more additional adjacent electrode contacts included in the plurality of electrode contacts.

8. The self-curling cochlear electrode lead of claim 6, wherein:
    a length of the first shape memory polymer element completely spans a first electrode contact included in the plurality of electrode contacts and partially spans a second electrode contact included in the plurality of electrode contacts, the first electrode contact being directly adjacent to the second electrode contact; and
    a length of the second shape memory polymer element partially spans the second electrode contact and completely spans a third electrode contact included in the plurality of electrode contacts, the second electrode contact being directly adjacent to the third electrode contact.

9. The self-curling cochlear electrode lead of claim 6, wherein the first shape memory polymer element and the second shape memory polymer element have different lengths in the longitudinal direction of the cochlear electrode lead.

10. The self-curling cochlear electrode lead of claim 6, wherein:
    the first shape memory polymer element has a first cross-sectional shape when viewed in a cross section that is perpendicular to the longitudinal direction of the cochlear electrode lead;
    the second shape memory polymer element has a second cross-sectional shape when viewed in an additional cross section that is perpendicular to the longitudinal direction of the cochlear electrode lead; and
    the first cross-sectional shape is different from the second cross-sectional shape.

11. The self-curling cochlear electrode lead of claim 6, wherein:
    the first shape memory polymer element has a first change in modulus of elasticity at the transition temperature;
    the second shape memory polymer element has a second change in modulus of elasticity at the transition temperature; and
    the first change in modulus of elasticity is different from the second change in modulus of elasticity.

* * * * *